United States Patent
Paufique

(10) Patent No.: US 11,648,196 B2
(45) Date of Patent: May 16, 2023

(54) ACTIVE INGREDIENT INCLUDING A BLACK OAT EXTRACT AND A SPINY RESTHARROW EXTRACT AND COSMETIC USES, IN PARTICULAR ANTI-GRAYING

(71) Applicant: SOCIETE INDUSTRIELLE LIMOUSINE D'APPLICATION BIOLOGIQUE, Objat (FR)

(72) Inventor: Jean Paufique, Objat (FR)

(73) Assignee: SOCIETE INDUSTRIELLE LIMOUSINE D'APPLICATION BIOLOGIQUE, Objat (FR)

( * ) Notice: Subject to any disclaimer, the term of this patent is extended or adjusted under 35 U.S.C. 154(b) by 186 days.

(21) Appl. No.: 17/183,798

(22) Filed: Feb. 24, 2021

(65) Prior Publication Data

US 2021/0259948 A1   Aug. 26, 2021

(30) Foreign Application Priority Data

Feb. 25, 2020   (FR) .................................. FR 2001842

(51) Int. Cl.

| | |
|---|---|
| A61K 8/9789 | (2017.01) |
| A61K 8/9794 | (2017.01) |
| A61Q 5/00 | (2006.01) |
| A61K 8/02 | (2006.01) |
| A61K 8/04 | (2006.01) |
| A61K 8/64 | (2006.01) |
| A61Q 5/02 | (2006.01) |
| A61Q 5/12 | (2006.01) |

(52) U.S. Cl.
CPC .......... *A61K 8/9789* (2017.08); *A61K 8/0216* (2013.01); *A61K 8/042* (2013.01); *A61K 8/64* (2013.01); *A61K 8/9794* (2017.08); *A61Q 5/02* (2013.01); *A61Q 5/12* (2013.01); *A61K 2800/805* (2013.01)

(58) Field of Classification Search
None
See application file for complete search history.

(56) References Cited

U.S. PATENT DOCUMENTS

2004/0202638 A1 * 10/2004 Takada ................... A61K 35/20
                                                            424/74
2019/0336884 A1    11/2019 Makerri et al.

FOREIGN PATENT DOCUMENTS

| CN | 108618133 A | 10/2018 |
| JP | 2002080382 A | 3/2002 |

* cited by examiner

*Primary Examiner* — Brian Gulledge
(74) *Attorney, Agent, or Firm* — Greer, Burns & Crain, Ltd.

(57) ABSTRACT

The invention relates to a cosmetic active ingredient comprising at least one extract of *Avena strigosa* and at least one extract of *Ononis spinosa*.
The invention also relates to a composition including it, a method for obtaining it and the use of this cosmetic active ingredient, in particular for its anti-graying effect on the hair.

20 Claims, 5 Drawing Sheets

ACTIVE INGREDIENT INCLUDING A BLACK OAT EXTRACT AND A SPINY RESTHARROW EXTRACT AND COSMETIC USES, IN PARTICULAR ANTI-GRAYING

CROSS-REFERENCE TO RELATED APPLICATIONS

This application claims priority to French patent application FR 2001842, filed Feb. 25, 2020.

FIELD OF THE INVENTION

The invention relates to a specific cosmetic active ingredient comprising at least one extract of *Avena strigosa* combined with at least one extract of *Ononis spinosa*, which is useful in cosmetics in particular for preventing and/or combating graying of the hair. The invention also relates to the cosmetic compositions including it, to a method for obtaining such an active ingredient as well as to its cosmetic uses, in particular on the hair.

PRIOR ART

Recent research has shown that the appearance of hair is a major attribute in interpreting a subject's age, health and attractiveness. The hair is thus a real tool of communication and seduction and has considerable power in building the identity and the image that a person wishes to convey.

In this context, the appearance of gray hair, called canities or graying of the hair, although a normal phenomenon occurring with aging, is unfortunately often distressing. A study has shown that salt-and-pepper hair ages women by 6 years relative to their real age, while men are perceived to be 3 years older. In a social environment where the imperatives of youth culture remain significant, gray hair transmits a biased image of aging and is sometimes perceived as carelessness, hence the legitimate desire to hide it.

However, currently, to hide gray hair, it is necessary to use hair dyes. As the latter remain restrictive, there is a great need for a product capable of making gray hair disappear and/or of preventing its appearance.

SUMMARY OF THE INVENTION

The objective of the invention is to meet this need by providing an active ingredient which is capable of reducing the number of gray hairs, in particular by promoting the re-pigmentation of the hair fiber and by improving the structural quality of the hair.

To this end, one subject of the invention is a cosmetic active ingredient comprising at least one extract of *Avena strigosa* and preferably also at least one extract of *Ononis spinosa*.

*Avena strigosa*, or black oats, is a cereal native to the western Mediterranean. It is a rustic cereal, cultivated in Europe for several millennia, in particular for the nutritional value of its seeds, which are rich in proteins and lipids. The cultivation of black oats alternating with other plants is appreciated for its allelopathic powers, which inhibit the development of unwanted plants, but also for its powerful root system, improving the structure of the soil. Once black oats are harvested, part of the fallow biomass provides organic matter in the soil (green manure) and fights against the development of phytoparasites.

*Ononis spinosa*, or spiny restharrow, is a shrub native to semi-arid meadows and pastures of Europe, Western Asia and North Africa. This small-sized plant is recognizable by its papilionaceous flowers, whose powdery pink corolla evokes the eponymous butterfly shape. It is a plant with strong roots. Restharrow roots are known for their diuretic and antilithiatic properties. In traditional medicine, they are used to stimulate diuresis, as well as for their analgesic and anti-bacterial properties. The valuation of restharrow is also a matter of artisanal know-how, as the plant was used in Iran to produce colors.

Now, surprisingly, when the extracts of *Avena strigosa* and of *Ononis spinosa* are applied to hair, they make it possible to effectively improve the fight against graying of the hair, both in prevention and in treatment.

The subject of the invention is therefore a particular cosmetic active ingredient, namely a cosmetic active ingredient comprising at least one extract of *Avena strigosa* and at least one extract of *Ononis spinosa*, as well as its cosmetic use in application to the hair, in order to improve an anti-graying effect.

A subject of the invention is also a method for obtaining such an active ingredient, as well as cosmetic compositions suitable for hair application including it.

Advantageously, the combined use of *Avena strigosa* and *Ononis spinosa* makes it possible to fight effectively against the oxidative stress of gray hair for a significant, visible and lasting anti-graying effect.

Other features and advantages will emerge from the detailed description of the invention which follows, done with reference in particular to the examples, test results and figures.

FIGURES

DEFINITIONS

Figure 1:
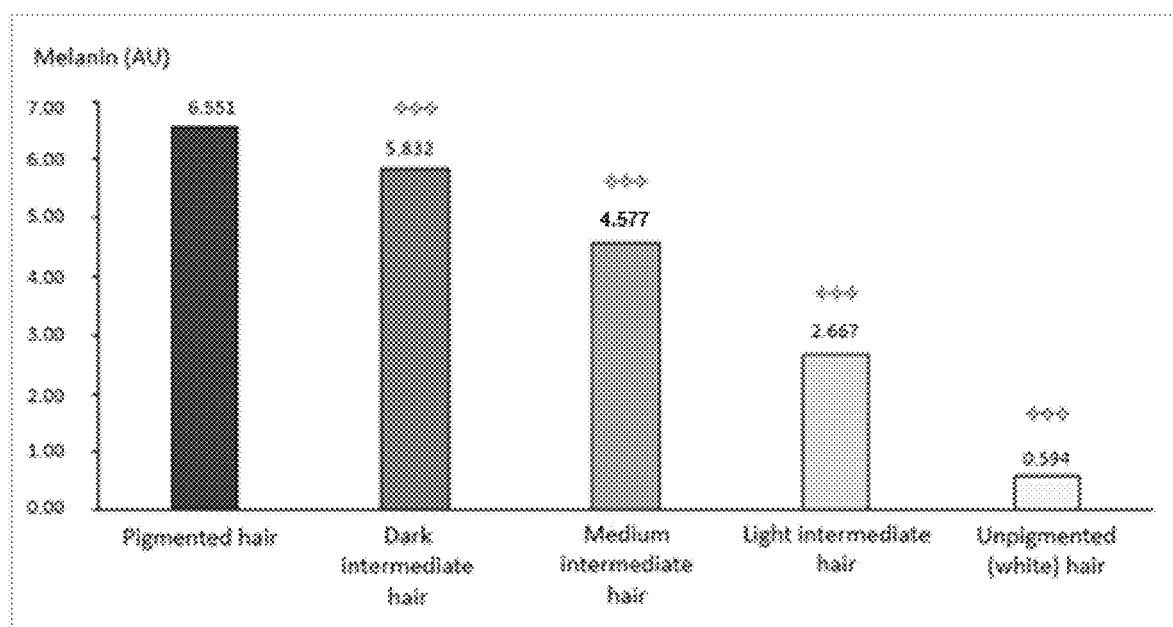
FIG. 1 shows the results of the evolution of melanin as a function of hair pigmentation in the modeling of the molecular signature of the graying of the hair.

Within the meaning of the invention, "cosmetic active" or "cosmetic active ingredient" means at least one molecule, preferably a set of molecules having a cosmetic effect on the skin or the hair.

Within the meaning of the present invention, "extract" of a raw material X means any molecule or mixture of at least two molecules obtained from a raw material X, regardless of the method of extraction of said molecule or molecules. It may for example be an extract obtained by aqueous and/or hydroalcoholic and/or hydroglycolic and/or hydrolysis extraction, etc.

Within the meaning of the invention, "hydrolyzate" of a raw material X means any extract obtained from a raw material X, by a method comprising at least one enzymatic or chemical hydrolysis step.

Within the meaning of the invention, "enzymatic hydrolyzate" of a raw material X means any extract obtained from a raw material X by a method comprising at least one enzymatic hydrolysis step.

Within the meaning of the invention, "hydroglycolic extract" of a raw material X means any extract obtained from a raw material X by a method comprising at least one extraction step using at least a mixture of at least two solvents (water and a glycolic solvent, such as for example butylene glycol).

DETAILED DESCRIPTION OF THE INVENTION

The invention therefore relates to a specific active ingredient, particularly useful in cosmetics.

Said active ingredient is a cosmetic active ingredient comprising at least one extract of *Avena strigosa* and at least one extract of *Ononis spinosa*.

Preferably, the cosmetic active ingredient according to the invention comprises at least one hydrolyzate of *Avena strigosa*. It may be an enzymatic hydrolyzate of *Avena strigosa*, in particular an enzymatic hydrolyzate obtained using one or more proteases.

Preferably, the active ingredient according to the invention comprises at least one extract of *Avena strigosa* obtained from seeds of *Avena strigosa*.

Preferably, the active ingredient according to the invention comprises at least one hydroglycolic extract of *Ononis spinosa*.

Preferably, the active ingredient according to the invention comprises at least one extract of *Ononis spinosa* obtained from roots of *Ononis spinosa*.

According to a preferred embodiment, the cosmetic active ingredient according to the invention comprises at least one extract of seeds of *Avena strigosa* and at least one extract of roots of *Ononis spinosa*.

Preferably, the cosmetic active ingredient according to the invention comprises at least one peptide fraction. Preferably, the peptide fraction of the active ingredient according to the invention comprises at least peptides with molar masses of less than 2000 Da. According to a particularly suitable embodiment, the peptides with molar masses of less than 2000 Da preferably represent between 21% and 53% by weight of dry matter of the active ingredient according to the invention, in particular about 30% by weight of dry matter of the active ingredient according to the invention (either 30% or 30% plus or minus 5%).

The assay of the peptides in the active ingredient according to the invention can be carried out in particular by the KJELDHAL method (reference: Official method of analysis of the A.O.C., 12th ed. W Horwitz, E. D., New York, 15-60, 1975). The protein content is expressed as a percentage relative to the dry matter content. In addition, in order to determine the size of the peptide compounds present in the active ingredient according to the invention, it is possible to carry out F.P.L.C.-type chromatography.

According to another aspect, the active ingredient according to the invention can comprise at least phenolic compounds, preferably at least phenolic acids and flavonoids. In the case where the active ingredient according to the invention comprises polyphenolic compounds, they can preferably represent between 11% and 29% by weight of dry matter of the active ingredient according to the invention, in particular approximately 22% by weight of dry matter of the active ingredient (either 22% or 22% plus or minus 5%).

The content of phenolic compounds can be determined by colorimetric assay. The phenolic compounds form, in the presence of potassium ferricyanide and iron chloride, colored complexes which can be determined by spectrophotometry at 715 nm. The intensity of this coloration is proportional to the quantity of phenolic compounds present in the sample. Calibration solutions are prepared from a hesperidin standard of 40 to 120 mg/L. A calibration curve of the optical densities of the calibration solutions as a function of their concentration is constructed. The samples are diluted beforehand with distilled water so that the polyphenol content corresponds to the calibration range. The amount of polyphenols in the samples is determined using the calibration curve.

The phenolic compounds of the active ingredient according to the invention can be characterized by any suitable method, in particular by liquid chromatography coupled with UV detection.

The active ingredient according to the invention can also contain carbohydrates and/or minerals.

The active ingredient according to the invention can thus comprise:
peptides, and/or
phenolic compounds and/or
carbohydrates, and/or
minerals.

Preferably, the active ingredient according to the invention comprises at least:
peptides (biopeptides) and phenolic compounds, and
possibly carbohydrates, and/or minerals.

The active ingredient according to the invention can be in solid form or in liquid form.

When it is in liquid form, the active ingredient according to the invention is preferably exclusively constituted by one or more liquid extracts of *Avena strigosa* and one or more liquid extracts of *Ononis spinosa*.

Preferably, the ratio of *Avena strigosa* extract/*Ononis spinosa* extract is between 45/55 and 55/45 by volume.

The active ingredient according to the invention in liquid form is preferably in the form of a limpid liquid, with a weak odor and an amber color. It can, however, have a stronger color and/or be discolored by any method known to a person skilled in the art.

Preferably, the active ingredient according to the invention in liquid form has a dry matter content of: 10 g/L to 50 g/L, even more preferably from 20 g/L to 32 g/L.

When the active ingredient is in solid form, particularly in the form of a powder, the active ingredient according to the invention is made up of:
a support such as for example maltodextrins, and
at least one extract of *Avena strigosa* and at least one extract of *Ononis spinosa*.

In this case, preferably, the extract or extracts represent at least 10% by weight of the active ingredient and the support represents no more than 90%.

The active ingredient according to the invention can also take the form of a dry film. In this case, the combination of extract of *Avena strigosa* and extract of *Ononis spinosa* preferably represents at least 0.1% by weight of the dry film.

The extract of *Avena strigosa* present in the active ingredient according to the invention can be obtained by any means. Preferably, the active ingredient according to the invention comprises at least one extract obtained by carrying out the following steps:
solubilizing *Avena strigosa*, preferably seeds of *Avena strigosa*, in water at a rate of at least 100 g/L performing enzymatic hydrolysis or hydrolyses, preferably using proteases, following the supplier's instructions, separating the soluble and insoluble phases by any means making it possible to separate an insoluble phase from the soluble phase, for example by centrifugation, filtration or decantation preferably inactivating the enzymatic activities by any means allowing the inactivation of the enzymatic activities, for example by heat treatment preferably performing successive filtration(s) making it possible to select the filtrate, for example by filter press, ultrafiltration, nanofiltration, optionally deodorizing or discoloring by adding a process adjuvant allowing deodorization or discoloration.

The extract of *Ononis spinosa* present in the active ingredient according to the invention can be obtained by any means. Preferably, the active ingredient according to the invention comprises at least one extract of *Ononis spinosa* obtained by carrying out the following steps:

solubilizing at least 100 g/L in a hydroglycolic solution, preferably a water/Butylene Glycol solution, preferably 50/50 (v/v)

separating the soluble and insoluble phases by any means making it possible to separate an insoluble phase from the soluble phase, for example decantation, filtration or centrifugation preferably performing successive filtration(s) making it possible to select the filtrate, for example by filter press, ultrafiltration, nanofiltration.

Preferably, the two liquid extracts are mixed together to obtain the active ingredient according to the invention in liquid form. Preferably, this mixing step is followed by one or more filtration steps.

An example of a method for obtaining an active ingredient according to the invention comprising at least one extract of *Avena strigosa* and at least one extract of *Ononis spinosa* is a method comprising the following steps:

a/ Solubilizing powdered seeds of *Avena strigosa* in water followed by several enzymatic hydrolyses (at least two hydrolyses) and enzymatic inactivation by heat treatment b/ Solubilizing powdered roots of *Ononis spinosa* in a Butylene Glycol/water mixture c/ Mixing products from steps a/ and b/, d/ Separating the soluble and insoluble phases, for example by decantation, e/ Filtration(s) to purify the active ingredient.

The active ingredient according to the invention has characteristics which allow its use in cosmetics, and in particular on the hair for an anti-graying effect.

The active ingredient according to the invention indeed advantageously has a detoxifying and protective action, and thus promotes re-pigmentation of the hair fiber and improves the structural quality of the hair. These biological effects result in a significant decrease in the number of gray hairs. The active ingredient according to the invention, applied to the hair, makes it possible to reduce the formation of free radicals and the oxidation of amino acids, and to detoxify the cell by activating autophagy. In addition to this anti-free radical and detoxifying action, which is linked in particular to the presence of specific peptides of the active ingredient, the active ingredient according to the invention also preferably exhibits a pro-pigmenting effect on gray hair in natural color, linked in particular to the presence specific phenolic compounds.

Hair is made up of two distinct anatomical structures:
the hair shaft, visible part that emerges from the surface of the skin;
the subcutaneous hair follicle.

The mechanisms responsible for hair pigmentation take place within the hair follicle. Thus, the wide variety of hair colors is the result of a mixture between two pigments named eumelanin (black-brown) and pheomelanin (brown-red-yellow). These two types of melanin are synthesized by melanocytes, specialized cells for melanogenesis, specifically in melanosomes, intracellular U) organelles dedicated to this biological phenomenon. Located at the dermal papilla of the hair follicle, the melanocytes transfer the melanosomes to the neighboring precortical keratinocytes, which differentiate and assemble to form the growing pigmented hair shaft.

During the growth phase, the various enzymatic reactions necessary for the synthesis of melanin generate large quantities of reactive oxygen species (ROS) including hydrogen peroxide ($H_2O_2$). Beyond this endogenous radical stress, the synthesis of free radicals is also stimulated by certain environmental factors (ultraviolet radiation, pollution). The hair follicle is therefore particularly exposed to the accumulation of these highly reactive molecules, which can damage cellular lipids and proteins. Thus, the oxidation of certain amino acids such as methionine alters protein structures, but also the functioning of enzymes involved in melanogenesis. Oxidative stress also leads to degradation of pigmentation via the death of melanocytes.

In this context, studies have recently highlighted the value of autophagy, a cellular detoxification mechanism, in the protection of melanocytes. This process is described for its ability to protect melanocytes from oxidative stress by degrading and eliminating non-functional proteins and organelles. Autophagy appears to be a major biological mechanism in maintaining cell homeostasis in the hair follicle.

Melanogenesis (or synthesis of pigments) is a phenomenon that occurs in melanocytes, specialized cells located in the hair follicle. Due to the production of free radicals, it causes oxidative stress, the intensity of which can be worsened by exposure to various environmental factors. This oxidative imbalance plays a major role in the depigmentation of the hair, since it is at the origin of an inactivation of the enzymes involved in melanogenesis and/or an induction of the death of melanocytes.

Thus, to protect against it, cells set up a first line of defense which is capable of eliminating free radicals and repairing the cellular damage caused. In the event of greater damage, a second line of defense involving autophagy leads to the elimination of defective elements and therefore to cellular detoxification. These recently revealed data attest to the important role played by autophagy in the hair's defense against radical stress. Although the impact of oxidative stress at the cellular level and its major implication in the graying of the hair are now understood, its consequences on the level of the hair shaft have never been studied.

Advantageously, the active ingredient according to the invention exhibits an anti-radical effect. In addition, beyond the management of free radicals, the active ingredient according to the invention is capable of activating the cellular detoxification induced by autophagy. This mechanism is a powerful process capable of sequestering and breaking down damaged proteins and intracellular U) organelles. Thus, the active ingredient according to the invention restores the oxidative balance of the hair by acting on two levels of defense: the fight against free radicals and autophagy, which are essential elements of the anti-graying strategy.

In addition, the applicants have demonstrated that beyond the radical problem, there is a modification of the molecular markers linked to the biomechanical properties (conformation of proteins) and to the barrier function (organization of lipids) in gray hair. Indeed, they used microspectroscopy to study the biological modifications occurring during graying by working directly on hair samples. Spectral measurements were thus carried out on three types of hair: pigmented, gray and non-pigmented. The bioinformatics processing of the data allowed the classification of the samples according to the degree of hair pigmentation but also the identification of 3 intermediate stages of graying invisible to the naked eye. Owing to this technology, the applicants carried out a more detailed analysis of the evolution of graying. Owing to this innovative approach, changes in the structural quality of hair during graying have been described for the first time.

Advantageously, the active ingredient according to the invention is capable of acting on the structural quality of gray hair and thus allows graying hair to regain its natural color.

Thus, by acting on the organization of lipids and the conformation of proteins, two parameters linked to the barrier function and the mechanics of the hair, the active ingredient according to the invention restores strength and resistance to gray hair.

The active ingredient according to the invention therefore has a multifunctional action which results in less noticeable graying of the hair and in the hair regaining its natural color and its original structural quality.

The subject of the invention is therefore the cosmetic use of a cosmetic active ingredient as described above, alone or in a cosmetic composition, on the hair, preventing and/or combating graying of the hair, in particular:
  to preserve hair pigmentation, and/or
  to improve the structural quality of the hair, and/or
  to reduce the number of gray hairs.

The active ingredients according to the invention are preferably used in cosmetic compositions comprising a cosmetically acceptable medium. These are compositions in different dosage forms, preferably suitable for application to the hair.

These compositions can be particularly in the form of oil-in-water emulsions, water-in-oil emulsions, multiple emulsions (water/oil/water or oil/water/oil) which may optionally be microemulsions or nanoemulsions, or in the form of solutions, suspensions, hydrodispersions, aqueous gels or powders.

They can be more or less fluid and come in the form of shampoo, hair gel, hair lotion, hair mask, hair conditioner, conditioner, hair cream or any other aspect of hair care or styling cosmetics.

They can be compositions comprising at least 0.1% of the liquid active ingredient according to the invention, preferably between 0.5 and 10% or comprising at least 0.01% of a solid active ingredient (preferably powder) according to the invention.

In addition to the active ingredient, these compositions comprise a physiologically acceptable and preferably cosmetically acceptable medium, i.e., one that does not cause sensations of discomfort for the user, such as redness, tightness, or tingling of the scalp.

As an additive, the compositions according to the invention may contain at least one compound selected from:

oils, which can be selected particularly from linear or cyclic, volatile or non-volatile silicone oils, vegetable oils and esters, vegetable butters;
  waxes such as ozokerite, polyethylene wax, beeswax, or carnauba wax,
  surfactants, whether non-ionic, anionic, cationic, or amphoteric,
  co-emulsifiers and other consistency agents, such as linear fatty alcohols,
  thickeners and/or gelling agents,
  humectants such as polyols like glycerin,
  dyes, preservatives, fillers,
  sequestrants,
  ethyl alcohol
  conditioning agents, such as guar, cationic polymers,
  vitamins: B5, B3, E, B6,
  minerals, such as zinc, copper,
  perfumes,
  and mixtures thereof, without this list being exhaustive.

Examples of such additives are cited particularly in the CTFA Dictionary (International Cosmetic Ingredient Dictionary and Handbook, published by the Personal Care Product Council).

Of course, a person skilled in the art would take care to select any additional compounds, active or non-active, and the quantity thereof such that the advantageous properties of the mixture are not, or not substantially, altered by the addition envisaged.

These compositions are intended in particular for use on hair, in particular gray hair or hair comprising gray hair, in particular for an anti-graying effect. A subject of the invention is therefore also a cosmetic method for the hair of a human being, for preventing and/or combating graying of the hair, which consists in applying to the hair, at least once a day, a composition comprising an active ingredient according to the invention.

In order to illustrate the cosmetic effects on gray hair of active ingredients according to the invention, examples and test results are presented below.

EXAMPLES

Example 1: Example of Active Ingredient According to the Invention in Liquid Form The active ingredient is obtained by implementing the following steps:
a/ implementing the following steps:
  Solubilizing seeds of *Avena strigosa* at a rate of 100 g/L,
  Performing hydrolyses using two different proteases, following the supplier's instructions
  Separating the soluble and insoluble phases
  Thermal inactivation
  Filtrations
  Deodorization
  Filtration
b/ implementing the following steps:
  Solubilizing *Ononis spinosa* at 200 g/L in a water/butylene glycol 50/50 (vol/vol) mixture
  Stirring
  Separating the soluble and insoluble phases by decantation
  Filtration
c/ Mixing products from steps a/ and b/,
d/ Separating the soluble and insoluble phases, for example by decantation
e/ Filtration(s) to concentrate the active ingredient The obtained active ingredient has the following analytical characteristics:
a dry matter content of 26.6 g/L,
a peptide content of 30.5% by weight of dry matter of the hydrolyzate (determined by the KJELDAHL method)
a total sugar content of 39% by weight of the dry matter of the hydrolyzate (calculated using a range of glucose)
a polyphenol content of 21.4% by weight of dry matter
8.3% ash by weight of dry matter (determined by weighing the residues from the incineration of the hydrolyzate samples at 550° C. in an electric muffle furnace).

Example 2: Example of a Conditioning Mask Composition According to the Invention An example of a formulation containing an active ingredient according to the invention is presented in Table 1 below. This mask is a hair treatment with a creamy texture that envelops the hair in softness from root to tip. It can be used as a nighttime mask, pre-shampoo treatment or conditioner. After rinsing, the hair is supple and shiny.

TABLE 1

| | Ingredients | INCI name | % |
|---|---|---|---|
| A | Water | Aqua (water) | q.s. 100 |
| | Preservative | — | q.s. |
| B | Incroquat behenyl TMS | Behentrimonium Methosulfate (and) Cetearyl Alcohol | 6.0 |
| | Cetyl alcohol | Cetyl alcohol | 1.5 |
| | Crodamol SS | Cetyl esters | 3.0 |
| | Shea Butter | *Butyrospermum parkii* (shea) butter | 0.75 |
| | Bioxan SFT50 | Tocopherol & *Helianthus annuus* (sunflower) seed oil | 0.05 |
| C | Plantacare 818 UP | Coco-glucoside & aqua (water) | 1.0 |
| D | Active ingredient of example 1 | Butylene glycol & Water & *Avena strigosa* seed extract & *Ononis spinosa* Root Extract | 2.5 |

It is obtained by carrying out the following procedure:
Place A under magnetic stirring and heat to 80° C.
Place B under magnetic stirring and heat to 80° C.
Under rotor-stator, emulsify B in A.
At 40° C., under moderate stirring, add C then D.

Example 3: Example of an Anti-Graying Shampoo Composition According to the Invention An example of a formulation containing an active ingredient according to the invention is presented in Table 2 below. This shampoo develops a creamy foam that gently cleanses the hair.

TABLE 2

| | Ingredients | INCI name | % |
|---|---|---|---|
| A | Purified Water | Aqua (water) | q.s. 100 |
| B | Carbopol Aqua SF1 | Aqua (water) & Acrylates copolymer | 2.0 |
| C | Texapon N70 | Sodium laureth sulfate & aqua (water) | 10.3 |
| D | Preservative | — | q.s. |
| E | Soda 28% | Sodium hydroxide & aqua (water) | q.s. pH 6.2-6.6 |
| F | Amonyl 675 SB | Cocamidopropyl Hydroxysultaine & aqua (water) | 5.0 |
| G | Rewoteric AM C | Sodium Cocoamphoacetate & aqua (water) | 8.0 |
| H | Oramix NS10 | Decyl glucoside & aqua (water) | 3.7 |
| I | Active ingredient of example 1 | Butylene glycol & Water & *Avenastrigose* seed extract & *Ononis spinoso* Root Extract | 2.5 |
| J | Citric acid solution 10% | Citric acid & aqua (water) | q.s. pH 5-5.5 |

It is obtained by carrying out the following procedure:
Scatter B in A.
Heat AB to 70° C. with magnetic stirring.
Add C to AB during heating.
At 70° C., add D in ABC.
Cool to room temperature with magnetic stirring.
Neutralize with E at pH 6.2-6.6.
Add F, G, H, and I.
Adjust the pH with J to pH 5-5.5.

Example 4: Example of Hair Lotion Composition According to the Invention

An example of a formulation containing an active ingredient according to the invention is presented in Table 3 below. Non-greasy and non-sticky, this lotion dries quickly and leaves hair supple without weighing it down.

TABLE 3

| | Ingredients | INCI name | % |
|---|---|---|---|
| A | Water | Aqua (water) | q.s. 100 |
| | Pentylene glycol | Pentylene glycol | 5.0 |
| | Butylene glycol | Butylene glycol | 10.0 |
| B | Ethanol | Alcohol | 15.0 |
| | Preservative | — | q.s. |
| C | Active ingredient of example 1 | Butylene glycol & Water & *Avena strigosa* seed extract & *Ononis spinosa* Root Extract | 2.5 |
| D | Citric acid solution 10% | Citric Acid | q.s. pH 4.8-5.2 |

It is obtained by carrying out the following procedure:
Place A under magnetic stirring.
Add B then C.
Adjust the pH between 4.8 and 5.2 with D.

Example 5: Example of Elixir De Jouvence Gel Composition According to the Invention An example of a formulation containing an active ingredient according to the invention is presented in Table 4 below. It is an ultra fresh gel that penetrates quickly to leave hair soft and silky without greasy residue.

| | Ingredients | INCI name | % |
|---|---|---|---|
| A | Water | Aqua (water) | q.s. 100 |
| | Pentylene glycol | Pentylene glycol | 5.0 |
| | Butylene glycol | Butylene glycol | 10.0 |
| B | Ethanol | Alcohol | 5.0 |
| | Preservative | — | q.s. |
| C | Carbopol Ultrez 20 | Acrylates/C10-30 Alkyl cacrylate crosspolymer | 0.15 |
| D | Soda 28% | Sodium hydroxide & aqua (water) | q.s. pH 5-5.5 |

-continued

| | Ingredients | INCI name | % |
|---|---|---|---|
| E | Active ingredient of example 1 | Butylene glycol & Water & Avena strigosa seed extract & Ononis spinosa Root Extract | 2.5 |

It is obtained by carrying out the following procedure:
Place A under magnetic stirring.
Add B in A.
Disperse C in AB.
Adjust the pH between 5.0 and 5.5 with D.
Add E.

Study of the Effectiveness of the Active Ingredient According to the Invention on the Graying of the Hair A. Modeling: Establishment of the Molecular Signature of the Graying of the Hair The objective of this study is to establish the molecular characteristics of gray hair.

Canities is a progressive and natural phenomenon occurring over time. The problem associated with the variation in the structure and the hygroscopic nature of gray hair is added to the problem of depigmentation. The lipid composition and the structure of the proteins making up the hair are associated with the structural quality of the hair shaft. To date, studies of hair lipids and proteins have mainly been done by comparing hair from different ethnic groups or by exposing the hair to external factors. Very few studies have focused on the evolution of these molecular markers during graying.

In this context, a study was carried out by Raman microspectroscopy on the surface of hair taken in vivo, in order to determine the various molecular modifications occurring in the non-pigmented, intermediate and pigmented fibers.

The operating protocol is described below.

Raman analysis was performed on 29 Caucasian volunteers, female or male, aged 33 to 65 years (mean age 52±9 years) and presenting a graying stage ranging from 1 to 8 on a scale from 0 to 10 over the entire head of hair (frontal and temporal area).

For each volunteer, the hair was taken (length of about 2 cm) and a selection was made as follows:
2 non-pigmented hairs (white);
2 to 5 intermediate hairs;
2 pigmented hairs.

The hairs are analyzed by Raman microspectrometer.

The spectral measurements obtained are used on the one hand to validate the type of hair by a hierarchical classification, and on the other hand to quantify the molecular descriptors of interest by type of hair.

In order to consolidate the classification of the different types of hair defined visually, groups were formed using an Ascending Hierarchical Classification (ACH) of Raman spectra.

On the basis of the groups defined previously, the average Raman spectra were calculated for each group.

The descriptors of interest selected are:
the amount of melanin;
the amount of hydrogen peroxide;
oxidation of amino acids;
the conformation of lipids;
the secondary structure of proteins.

First, an analysis of the amount of melanin was performed. This analysis makes it possible to determine the quantity of melanin for each group of hair established according to the classification proposed above. The results are presented in FIG. 1, which shows an evolution of the melanin as a function of the pigmentation of the hair.

These results show that the amount of melanin decreases with depigmentation of the hair. Indeed, a number of factors are involved in the progressive alteration of melanogenesis, which leads to the gradual appearance of hair fibers with a low pigment content (gray hair) or with a total absence of pigment (non-pigmented, white hair).

Hair oxidation analysis was also performed: hydrogen peroxide analysis and oxidized amino acid analysis. The gradual decrease in pigment production is largely caused by the presence of reactive oxygen species (ROS) in the hair follicle. The accumulation of hydrogen peroxide contributes in particular to the death of melanocytes in the hair follicle. This oxidative stress is also measured at the level of the hair shaft, as demonstrated by this study evaluating the molecules that attest to hair oxidation.

Figure 2:
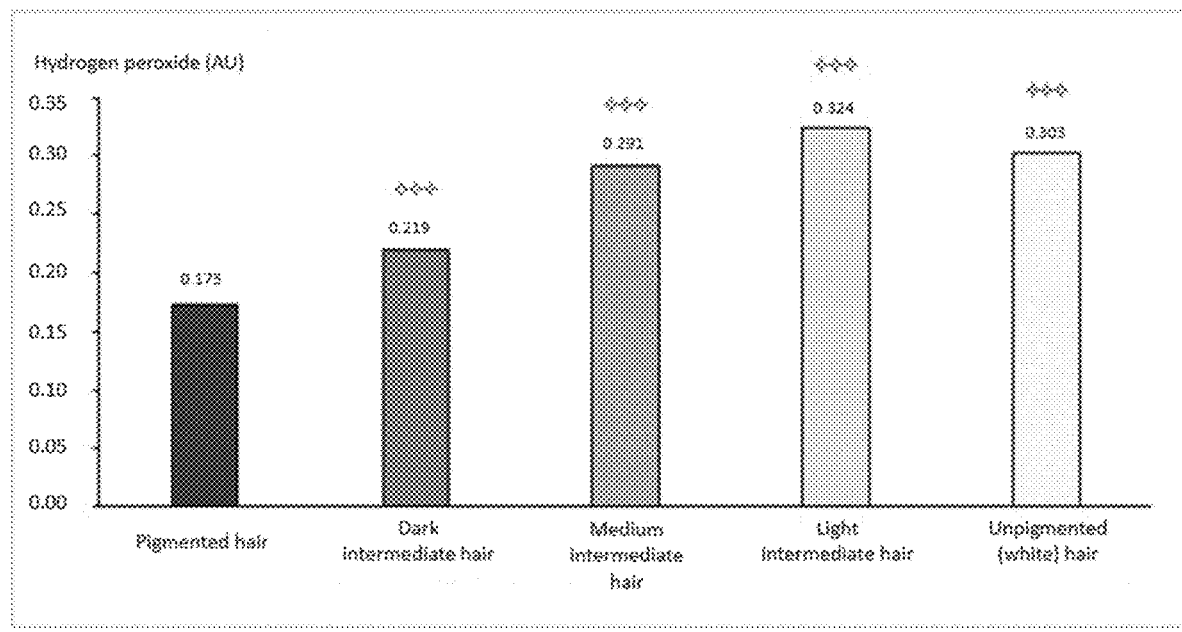
FIG. 2 shows the results of the analysis of hydrogen peroxide in the modeling of the molecular signature of the graying of the hair.

The hydrogen peroxide analysis consists in determining the evolution in the quantity of hydrogen peroxide for each group of hair established according to the classification proposed above. The results are presented in FIG. 2, which shows the evolution in the quantity of hydrogen peroxide as a function of the pigmentation of the hair. It is observed that the quantity of hydrogen peroxide increases with the depigmentation of the hair. These results demonstrate the accumulation of hydrogen peroxide in gray and unpigmented (white) hair.

Figure 3:
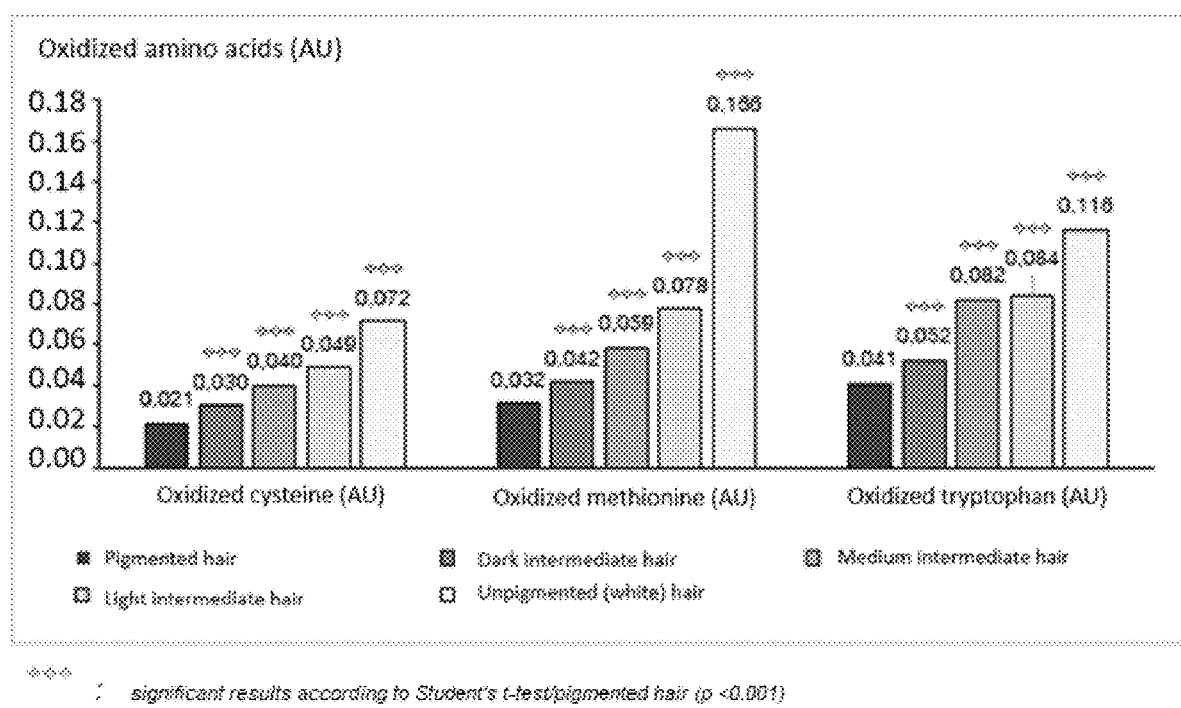
FIG. 3 shows the results of the analysis of oxidized amino acids in the modeling of the molecular signature of the graying of the hair.

The analysis of oxidized amino acids consists in determining the evolution of the quantity of oxidized amino acids for each group of hair established according to the classification proposed above. The results are presented in FIG. 3, which shows the evolution of the oxidized amino acids as a function of the pigmentation of the hair. It is observed that the oxidation of the proteins increases with the depigmentation of the hair. This is because the oxidized amino acids that make up keratin, namely cysteine, tryptophan, and methionine, are all present in high levels in unpigmented hair.

In addition to these analyses, an analysis of markers related to the structural quality of hair was performed, namely a secondary structure analysis of the proteins and an analysis of the conformation of the lipids.

Figure 4:
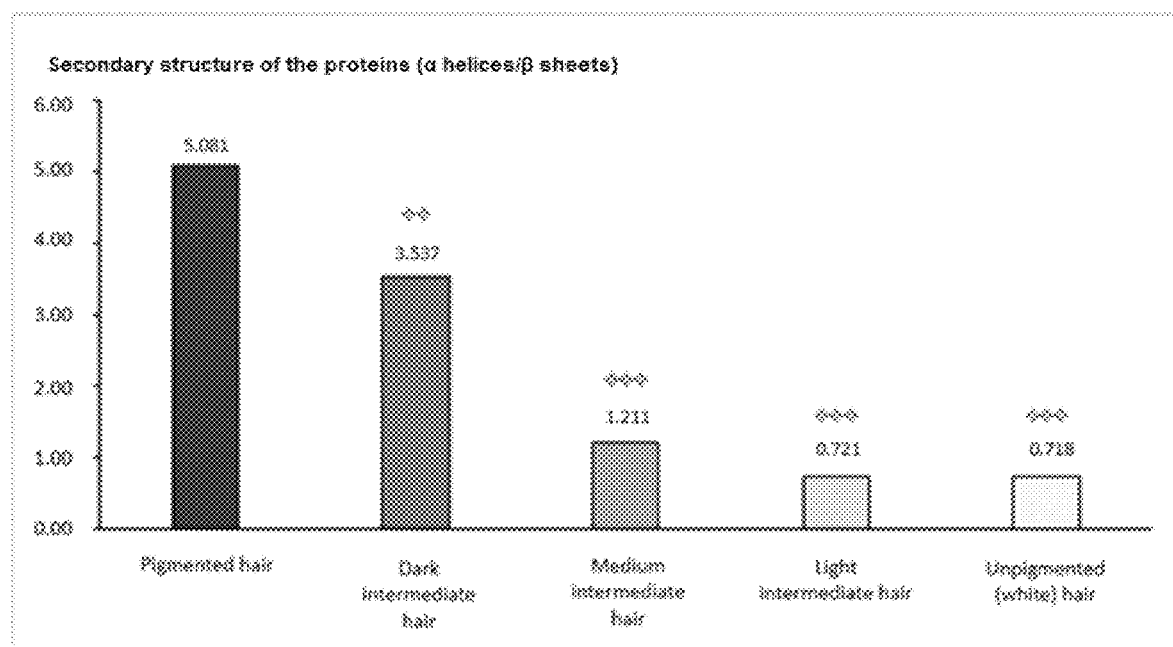
FIG. 4 shows the results of the analysis of the secondary structure of proteins (a helices/(3 sheets) in the modeling of the molecular signature of the graying of the hair.
Figure 5:
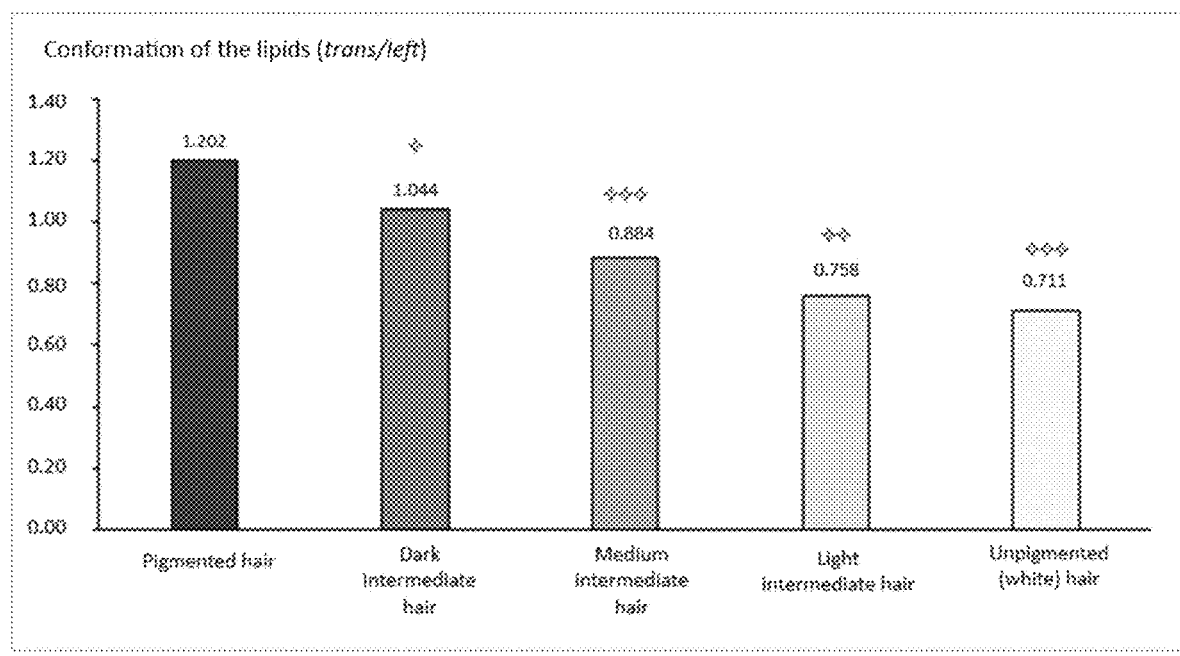
FIG. 5 shows the results of the analysis of the conformation of the lipids in the modeling of the molecular signature of the graying of the hair.

First of all, an analysis of the secondary structure of the proteins (α helices/β sheets) was carried out. The protein secondary structures of pigmented hair are mainly in the form of α helices, which gives them the ability to deform plastically without breaking (strength/ductility). The analysis of the secondary structure of the proteins consists in determining the evolution of the protein secondary structure for each group of hair established according to the classification proposed above. The results are presented in FIG. 4, which shows the evolution in the α helix/β sheet ratio as a function of the pigmentation of the hair. It is observed that the protein secondary structures in a helices decrease with depigmentation of the hair compared to the β sheets, which increase. This results in an alteration of the biomechanical properties of gray hair.

A lipid conformation analysis was performed. The lipids of pigmented hair mainly exhibit a trans conformation. This conformation allows good lipid organization, which is a key element for maintaining impermeability and hydrophobicity at the surface of the fibers. The capillary lipid barrier is therefore intimately linked to the lipid conformation (compactness) in the cuticle. The analysis of the lipid conformation makes it possible to determine the evolution of the lipid conformation for each group of hair established according to the classification proposed above. The results are presented in FIG. 4, which shows the evolution in the trans/left ratio as a function of the pigmentation of the hair. It is observed that the lipids in the trans conformation decrease with depigmentation of the hair, while those in the left conformation increase. The changes in lipid conformation observed with hair depigmentation attest to a decrease in the barrier function at the hair fiber.

B. Study of the Antioxidant and Detoxifying Effect of the Active Ingredient According to the Invention The objective of this study is to evaluate the antioxidant and detoxifying effect of an active ingredient according to the invention by its capacity to:
- limit the production of reactive oxygen species (ROS);
- promote autophagic activity;
- reduce the oxidation of amino acids in the hair fiber.

Graying of the hair is perceived as a sign of aging and can significantly impact the image that is reflected. Although the mechanisms responsible for this loss of pigmentation are not yet fully understood, this graying appears to be due to a dysfunction and rarefaction of the melanocytes of the hair follicle which can be attributed to the harmful effects of ROS. In fact, follicular melanocytes are constantly subjected to a high level of oxidative stress linked to melanogenesis and to their daily exposure to environmental factors such as pollution or UV rays. However, with age, their ability to cope with this oxidation diminishes. Various studies have underlined a weakening of the anti-oxidant system and a progressive accumulation of ROS, in particular hydrogen peroxide ($H_2O_2$), in the gray hair follicles.

Among the processes set up by the cell to fight against oxidative stress, autophagy plays a major role by allowing the elimination of damaged organelles. In this sense, a study has revealed the importance of autophagy in the protection of melanocytes against damage induced by exposure to $H_2O_2$.

Fighting against oxidative stress and its harmful effects (i.e. oxidation of amino acids) in the hair follicle by limiting the production of ROS and promoting the activation of autophagy can be considered an interesting and innovative strategy to counteract graying of the hair.

For this study, different models were set up and different parameters were evaluated:
- ROS production and autophagy activity were quantified using specific fluorescent probes respectively analyzed by flow cytometry or confocal microscopy on human melanocytes subjected to oxidative stress;
- the amounts of $H_2O_2$ and oxidized amino acids were evaluated by Raman microspectroscopy on hair from volunteers.

The operating protocol for analyzing ROS production by human melanocytes is described below.

On D0, normal human keratinocytes are seeded and incubated at 37° C. in an atmosphere containing 5% $CO_2$ for several days.

On D1, the human melanocytes are treated with the active ingredient of Example 1 at 0.025% and 0.050% (V/V).

On D2, the human melanocytes are recovered and incubated for 30 minutes with the DCFDA probe. The melanocytes are treated with an $H_2O_2$ solution in the presence of the active ingredient according to the invention at 0.025% and 0.050% (V/V).

The production of ROS by the melanocytes is then analyzed by flow cytometry.

The production of ROS is proportional to the intensity of fluorescence present in the cells. Quantitative analysis was performed using a flow cytometer (FC500 MPL, Beckman Coulter). The acquisition and analysis are carried out using MXP acquisition and CXP analysis software (Beckman Coulter). The mean fluorescence intensity is expressed in arbitrary units (AU).

The results are shown in Table 5.

TABLE 5

|  | Quantity of ROS (AU) | Ability to limit ROS production (%) |
|---|---|---|
| Normal human melanocytes | | |
| Control | 13.16 | |
| Human melanocytes subjected to oxidative stress | | |
| Control | 40.07^^^ | |
| Example 1 at 0.025% | 37.18*** | 11 |
| Example 1 at 0.050% | 33.47*** | 25 |

^^^significant result according to Student's t-test/normal melanocytes control ($p < 0.001$)
***significant results according to Student's t-test/stressed melanocytes control ($p < 0.001$)

The operating protocol for analyzing the activation of autophagy by human melanocytes is described below.

On D0, normal human keratinocytes are seeded and incubated at 37° C. in an atmosphere containing 5% $CO_2$ for several days.

On D2, the human melanocytes are treated with an $H_2O_2$ solution. After stress, the melanocytes are treated with the active ingredient of Example 1 at 0.025% and 0.050% (V/V).

Then, the human melanocytes are labeled with a fluorescent probe making it possible to detect the autophagy vesicles.

The level of autophagy is proportional to the intensity of green fluorescence present in the cells. A quantitative analysis of the images was performed using Matlab® software. The mean fluorescence intensity per cell is expressed in arbitrary units (AU).

The results are shown in Table 6.

TABLE 6

|  | Amount of autophagy vesicles (AU) | Ability to activate autophagy (%) |
|---|---|---|
| Normal human melanocytes | | |
| Control | 919 | |
| Human melanocytes subjected to oxidative stress | | |
| Control | 4395^^ | |
| Example 1 at 0.025% | 5306 | 21 |
| Example 1 at 0.050% | 7773* | 77 |

^^significant result according to Student's t-test/normal melanocytes control ($p < 0.01$)
*significant result according to Student's t-test/stressed melanocytes control ($p < 0.05$)

The operating protocol for analyzing the quantity of $H_2O_2$ and of oxidized amino acids on hair obtained from volunteers is described below.

Raman analysis was performed on 10 Caucasian volunteers, female or male, aged 33 to 65 years (mean age 50±10 years), presenting a graying stage ranging from 2 to 8 on a scale from 0 to 10 over the entire head of hair (frontal and temporal area). The volunteers applied the active ingredient of Example 1 formulated at 2.5% in a lotion, for 6 months.

The collected hair (length of about 2 cm) is analyzed.

The ability of the active ingredient according to the invention to reduce oxidative stress on the scale of the hair shaft was evaluated using the following descriptors:

- the band at 875 cm$^{-1}$ is used to quantify the hydrogen peroxide ($H_2O_2$) present in the hair by Raman spectroscopy. High values of this band are associated with high oxidative stress.
- the S—O bands witness the oxidation of sulfur amino acids (oxidized cysteine: 1030 cm-1, oxidized methionine: 1040 cm-1) and oxidized tryptophan (kynurenine): 1050 cm-1. Bleaching of the hair shows an increase in these bands.

The obtained results show, after 4 months of application of the active ingredient according to the invention:
- an 18% decrease in the overall quantity of hydrogen peroxide contained in the hair,
- a 31% decrease in oxidized cysteine contained in the hair,
- a 35% decrease in oxidized methionine contained in the hair, and
- a 26% decrease in oxidized tryptophan contained in the hair.

The obtained results show, after 6 months of application of the active ingredient according to the invention:
- a 19% decrease in the overall quantity of hydrogen peroxide contained in the hair,
- a 31% decrease in oxidized cysteine contained in the hair,
- a 36% decrease in oxidized methionine contained in the hair, and
- a 30% decrease in oxidized tryptophan contained in the hair.

Thus all of these results show that:
- tested at 0.050% on human melanocytes subjected to oxidative stress, the active ingredient according to the invention significantly limits the production of ROS by 25% and activates autophagy by 77%.
- after 4 months of application, the active ingredient according to the invention is formulated at 2.5% significantly decreases, in the hair shaft, the amounts of hydrogen peroxide (−18%) and oxidized amino acids (oxidized cysteine: −31%; oxidized methionine: −35% and oxidized tryptophan: −26%). This effect is maintained after 6 months of daily application.

All of these data demonstrate the strong antioxidant and detoxifying potential of the active ingredient according to the invention.

C. Study of the Cryoprotective Effect of the Active Ingredient According to the Invention The objective of this study is to evaluate the capacity of an active ingredient according to the invention to maintain the viability of human melanocytes following oxidative stress.

Graying is characterized by a loss of pigment in the hair shaft which can in part be attributed to a depletion of follicular melanocytes. In fact, canities is accompanied by an excessive production of free radicals by the melanocytes, a phenomenon that can compromise their viability.

Preserving the viability of melanocytes in the face of oxidative stress is a strategy of choice to avoid their decline with age and to fight against graying of the hair.

The viability of human melanocytes following oxidative stress was assessed by flow cytometry.

The operating protocol of the study is described below.

On D0, normal human keratinocytes are seeded and incubated at 37° C. in an atmosphere containing 5% $CO_2$ for several days.

On D1, the human melanocytes are treated with the active ingredient of Example 1 at 0.025% and 0.050% (WV).

On D2, the human melanocytes are treated with a solution of $H_2O_2$ in the presence of the active ingredient of Example 1 at 0.025% and 0.050% (V/V).

After the stress, the melanocytes are again treated for 24 hours with the active ingredient of Example 1 at 0.025% and 0.050% (V/V).

On D3, the melanocytes are recovered and incubated with annexin V coupled FITC and propidium iodide.

The viability of the melanocytes is analyzed by flow cytometry using annexin V/propidium iodide double labeling.

These two reagents make it possible to distinguish between viable cells and cells progressing through cell death pathways (apoptosis, necrosis):
- apoptosis is demonstrated by specific binding of annexin V coupled to a fluorophore. In a healthy cell, phosphatidylserines are located only on the inner side of the plasma membrane. As soon as a U) cell goes into apoptosis, they are delocalized and expressed on both sides of the membrane. Annexin V is capable of labeling apoptotic cells by virtue of its strong affinity for phosphatidylserines.
- propidium iodide (PI) is a DNA intercalator capable of marking the nucleus of cells that have lost their membrane integrity. This phenomenon is characteristic of necrosis or late apoptosis.

Viable melanocytes are not labeled: they are negative for annexin V labeling and for PI labeling.

The percentage of viable melanocytes is measured using a flow cytometer (FC500 MPL, Beckman Coulter). For each condition, an identical number of events is analyzed (10,000 cells). The percentage of viable melanocytes corresponds to the proportion of melanocytes negative for annexin V and PI relative to the total number.

The acquisition and analysis are carried out using MXP acquisition and CXP analysis software (Beckman Coulter).

The results are shown in Table 7.

TABLE 7

| | Viable melanocytes (%) | Ability to protect melanocytes (%) |
|---|---|---|
| Normal human melanocytes | | |
| Control | 86.83 | |
| Human melanocytes subjected to oxidative stress | | |
| Control | 66.78^^^ | |
| Example 1 at 0.025% | 77.14 | 52 |
| Example 1 at 0.050% | 84.48*** | 88 |

^^^significant result according to Student's t-test/normal melanocytes control ($p < 0.001$)
***significant result according to the Student's t-test/stressed melanocytes control ($p < 0.001$)

It is observed that tested at 0.050% in the face of oxidative stress, the active ingredient according to the invention significantly preserves the viability of the melanocytes by 88% and thus exhibits a cytoprotective effect.

D. Study of the Pigmenting Effect of the Active Ingredient According to the Invention The objective of this study is to evaluate the capacity of an active ingredient according to the invention to stimulate the production of melanin.

The melanocytes responsible for hair pigmentation are located in the bulb of the hair follicles. These melanocytes produce and transfer melanin in the form of melanosomes to the precortical keratinocytes of the hair shaft. The perception of gray hair comes from the effect of mixing pigmented and unpigmented hair. However, individual hair fibers can exhibit a gradual dilution of their pigments and therefore different levels of graying. This dilution is linked to a reduction in the production of melanin, caused in particular by the alteration of enzymes involved in melanogenesis or by the death of melanocytes.

The production of melanin was assessed by:
- assay on human melanocytes subjected to oxidative stress;
- immunohistochemistry on hair follicles ex vivo (Warthin-Starry staining);
- Raman microspectroscopy on hair from Caucasian volunteers.

The operating protocol of the study for analyzing the production of melanin by human melanocytes is described below.

On D0, normal human keratinocytes are seeded and incubated at 37° C. in an atmosphere containing 5% $CO_2$ for several days.

On D1, the human melanocytes are treated with the active ingredient of Example 1 at 0.025% and 0.050% (V/V).

On D3, the human melanocytes are treated with a solution of $H_2O_2$ in the presence of the active ingredient of Example 1 at 0.025% and 0.050% (V/V).

After the stress, the melanocytes are treated again for 24 hours with the active ingredient of Example 1 at 0.025% and 0.050% (V/V).

On D4, the cells are recovered, counted with a view to assaying melanin.

The cell pellets are lysed in a sodium phosphate buffer supplemented with Triton X-100. The cell lysates are centrifuged and then dissolved in an NaOH solution to allow the melanin assay. The level of melanin is then quantified by spectrophotometric reading at 490 nm using a spectrophotometer. The results are shown in Table 8.

TABLE 8

| | Melanin production ($g/10^6$ cells) | Ability to increase melanin production (%) |
|---|---|---|
| Normal human melanocytes | | |
| Control | 32.44 | |
| Human melanocytes subjected to oxidative stress | | |
| Control | 23.93^^^ | |
| Example 1 at 0.025% | 26.66* | 32 |
| Example 1 at 0.050% | 34.76*** | 127 |

^^^significant result according to the signed ranks test/normal melanocytes control $p < 0.001$
*significant result according to the signed ranks test/stressed melanocytes ($p < 0.05$)
***significant result according to the signed ranks test/stressed melanocytes control ($p < 0.001$)

The operating protocol of the study for analyzing the production of melanin in the hair follicles ex vivo is described below.

This study was carried out according to the ex vivo hair follicle culture model developed by Philpott R) et al. The capacity of an active ingredient according to the invention to stimulate melanin production was evaluated by Warthin-Starry staining. This analysis was carried out exclusively on hair follicles in the anagen phase. The anagen phase of hair follicles was monitored via analysis of Ki-67 synthesis by immunohistofluorescence. This study was conducted on hair follicles from scalp fragments from 2 donors (23 and 33 years old).

On D0, The hair follicles are isolated from fragments of the scalp and incubated in culture medium at 37° C. in an oven containing 5% $CO_2$.

On D1, The hair follicles are photographed and measured on an IX 70 microscope (Olympus), coupled to an image analysis system (NIS-Elements software, Nikon). The hair follicles in the anagen phase are selected and treated with the active ingredient according to the invention of Example 1 at 0.10% (final V/V).

On D4, the hair follicles are photographed using an IX 70 microscope (Olympus) coupled to an image analysis system (NIS-Elements software, Nikon).

The follicles are then recovered and included in Tissue-Tek® and then frozen. Sections (6 μm) are made using a CM1850 cryostat (Leica) and then fixed.

Warthin-Starry staining is performed in order to visualize the melanin content of the hair follicles. Melanin corresponds to the black grains present on the sections after staining.

This staining is carried out with the Warthin-Starry staining kit (Abcam), following the supplier's instructions.

The cells of the hair follicle are demonstrated by pink staining with a solution of nuclear fast red (Abcam) following the supplier's instructions.

The melanin content was analyzed in standardized regions of interest (ROI) adapted to each follicle. The morphological landmarks used for the positioning of the ROIs are: the Auber line (virtual line crossing the dermal papilla at its widest part) and the junction between the external epithelial sheath and the conjunctive sheath. FIG. 19. Diagram of the image processing carried out to analyze U) the amount of melanin on hair follicles by Whartin-Starry staining.

An automatic quantitative analysis was performed using Matlab® software. The melanin content corresponds to the area occupied by melanin over the total area of the reference zone. The melanin content is expressed in arbitrary units (AU).

The results are shown in Table 9.

TABLE 9

| | Melanin content (AU) | Increased melanin production (%) |
|---|---|---|
| Human hair follicles ex vivo | | |
| Control | 0.186 | |
| Example 1 at 0.10% | 0.257* | 38 |

*significant result according to Student's t-test/hair follicles control ($p < 0.05$)

The operating protocol of the study for the analysis of the amount of melanin in hair from Caucasian volunteers is described below.

Raman analysis was performed on 10 Caucasian volunteers, female or male, aged 33 to 65 years (mean age 50±10 years), presenting a graying stage ranging from 2 to 8 on a scale from 0 to 10 over the entire head of hair (frontal and temporal area). The volunteers applied the active ingredient of Example 1 formulated at 2.5% in a lotion, for 6 months.

The hairs taken (length of approximately 2 cm) are analyzed with the Raman microspectrometer (LabRam Evolution, Horiba).

The capacity of the active ingredient according to the invention to reduce the quantity of melanin was evaluated using the following descriptor: the band at 1580 $cm^{-1}$ is used to quantify the melanin present in the hair by Raman spectroscopy. High values of this band are associated with a large amount of melanin.

There is an overall increase in the melanin contained in the hair from volunteers of 41% after 4 months of treatment and of 40% after 6 months of treatment.

Thus all of these results show that:
Tested at 0.050% on human melanocytes subjected to oxidative stress, the active ingredient according to the invention significantly increases the production of melanin by 127%,
Tested at 0.10% on human hair follicles, the active ingredient according to the invention significantly stimulates the production of melanin by 38%.
After 4 months of application, the active ingredient according to the invention formulated at 2.5% in a lotion significantly increases the amount of melanin in gray hair by 41%.
This effect is maintained after 6 months of daily application (+40%)
All of these data demonstrate the pigmenting effect of an active ingredient according to the invention.

E. Study of the Effect of the Active Ingredient According to the Invention on the Structural Quality of the Hair The objective of this study was to evaluate the effect of an active ingredient according to the invention on the protein secondary structures and the conformation of lipids, in Caucasian hair taken after 4 and 6 months of daily treatment.

Molecularly, the hair shaft is made up primarily of keratin-like proteins, lipids, melanin, and water. Keratin-like proteins organize themselves into bundles that make up the capillary cortex. The α helices are, with the β sheets, examples of secondary structures which locally determine the spatial conformation of the peptide chain. At the hair level, proteins are mainly α helices, a structure that contributes to the physical and mechanical properties as well as to the structural stability of the hair fiber. In gray hair, the α helix/β sheet ratio decreases, which results in an alteration in the biomechanical properties of the hair.

Lipids also play a fundamental role in the hair, since they constitute a matrix whose specific organization maintains the tightness of the cuticle. Lipids in trans conformation ensure the functionality of the hair barrier. In gray hair, the trans/left ratio decreases, which reflects a lipid disorganization as well as the degradation of the capillary barrier function.

The operating protocol of the study is described below.

Raman analysis was performed on 10 Caucasian volunteers, female or male, aged 33 to 65 years (mean age 50±10 years), presenting a graying stage ranging from 2 to 8 on a scale from 0 to 10 over the entire head of hair (frontal and temporal area). The volunteers applied an active ingredient according to the invention formulated at 2.5% in a lotion, for 6 months.

The collected hair (length of approximately 2 cm) is analyzed with the Raman microspectrometer (LabRam HR Evolution, Horiba).

For each volunteer and at each measurement time:
15 hairs are selected at random;
5 Raman measurement points are made on the surface of each hair.

The capacity of an active ingredient according to the invention to increase the α helix/β sheet ratio of proteins and the trans/left ratio of lipids was evaluated using the following descriptors:

The α helix/β sheet ratio (1650/1670 $cm^{-1}$) provides information on the secondary structure of the proteins. The predominance of the α helix structural conformation is linked to a good resistance of the hair fiber to mechanical deformations.

The trans vCC/left vCC ratio (1130/1080 $cm^{-1}$) provides information on the intramolecular conformation of the lipids. The spectral region of the CC elongations (1080-1130 cm-1) gives information on the conformation of lipids. The predominance of the trans conformation is related to a high compactness of the lipid barrier. Conversely, a high quantity of left conformers reflects a weakening of the compactness of the lipid structures of the hair The results corresponding to the effect of the active ingredient of Example 1 formulated at 2.5% in a lotion, on the α helix/β sheet ratio of the proteins, show an increase of 34% after 4 months of treatment and show an increase of 37% after 6 months of treatment.

The results corresponding to the effect of the active ingredient of Example 1 formulated at 2.5% in a lotion, on the trans/left lipid ratio, show an increase of 25% after 4 months of daily treatment and show an increase of 33% after 6 months of treatment.

By increasing the predominance of secondary structures in α helices (linked to a better organization of protein structures on the mechanical level) and lipids in trans conformation (linked to a higher compactness of the lipid structures and a good barrier function), the active ingredient according to the invention improves the structural quality of the hair.

F. Study of the Effect of the Active Ingredient According to the Invention on the Proportion of Gray Hair During this study, the in vivo effect of an active ingredient according to the invention formulated at 2.5% in a lotion on the evolution of the proportion of gray hair in Caucasian and Asian subjects was evaluated after 4 and 6 months of daily treatment.

The Caucasian panel was composed of 32 healthy volunteers, female or male, aged 33 to 65 years (mean age 52±9 years), and presenting a graying stage ranging from 1 to 8 on a scale from 0 to 10 over the entire head of hair (frontal and temporal area).

The Asian panel consisted of 17 healthy volunteers, female or male, aged 37 to 61 years (mean age 51±8 years), presenting a graying stage between 2 and 5 on a scale of 1 to 9 and a canities established for at least 10 years.

All of the volunteers applied the active ingredient according to the invention for 6 months, only in the evening, to the whole of the hair and the scalp.

The capacity of the active ingredient according to the invention to reduce the proportion of gray hair was evaluated, at the various times of the study, using the following methods:

1/ On the Caucasian panel:
Counting of gray hair on dermatoscopic acquisitions of the scalp carried out using a Trichoscan HD (Tricholog GmbH).
Blind rating of the graying stage on photographs taken on the frontal area by a jury of experts using a score scale (11 stages ranging from 0 to 10).

2/ On the Asian panel:
Scoring by clinical scoring of the density of white hair by a dermatologist directly on volunteers, using a score scale (Stage 1 to 9).

The results obtained on the Caucasian panel are presented below.

The results of the blind scoring show that after 4 months of daily application, the active ingredient according to the invention, formulated at 2.5% in a lotion, significantly reduced the number of gray hairs by 9% (p=0.0068). This effect continues after 6 months of application to reach a reduction of 12% (p=0.0045), i.e. an average reduction of 8 gray hairs/$cm^2$.

The results of the scoring by clinical scoring show that after 4 months of daily application, the active ingredient according to the invention formulated at 2.5% in a lotion significantly reduces the graying stage by 20% (p<0.001), corresponding to an average decrease of 1 graying stage. 91% of the volunteers showed a reduction in the graying stage. This effect is maintained after 6 months of daily application, with a decrease of 18% (p<0.001). An improvement in the graying stage was observed in 94% of the volunteers.

The results obtained on the Asian panel are presented below.

The results of the blind scoring show that after 4 months of daily application, the active ingredient according to the invention formulated at 2.5% in a lotion significantly reduces the graying stage by 7% (p=0.0359). This effect is maintained after 6 months of daily application, with a decrease of 7% (p=0.0359).

The invention claimed is:

1. A cosmetic active ingredient comprising at least one extract of *Avena strigosa* and at least one extract of *Ononis spinosa*.

2. The cosmetic active ingredient according to claim 1, characterized in that it comprises at least one extract of seeds of *Avena strigosa* and at least one extract of roots of *Ononis spinosa*.

3. The cosmetic active ingredient according to claim 1, characterized in that it comprises at least peptides.

4. The cosmetic active ingredient according to claim 1, characterized in that it comprises at least peptides with molar masses less than 2000 Da.

5. The cosmetic active ingredient according to claim 1, characterized in that the peptides with molar masses less than 2000 Da represent at least 30 wt. % dry matter of the active ingredient.

6. The cosmetic active ingredient according to claim 1, characterized in that it comprises at least phenolic compounds.

7. The cosmetic active ingredient according to claim 1, characterized in that it comprises at least phenolic acids and flavonoids.

8. The cosmetic active ingredient according to claim 1, characterized in that the phenolic acids and the flavonoids represent at least 22 wt. % dry matter of the active ingredient.

9. The cosmetic active ingredient according to claim 1, characterized in that the extract of *Avena strigosa* is a hydrolyzate of *Avena strigosa*.

10. The cosmetic active ingredient according to claim 1, characterized in that the extract of *Ononis spinosa* is a hydroglycolic extract of *Ononis spinosa*.

11. The cosmetic active ingredient according to claim 1, characterized in that the ratio of *Avena strigosa* extract/*Ononis spinosa* extract is between 45/55 and 55/45 by volume.

12. The cosmetic active ingredient according to claim 1, characterized in that it is in liquid form or in solid form.

13. The cosmetic active ingredient according to claim 1, wherein the cosmetic active ingredient is useful for preventing and/or combating graying of the hair.

14. The cosmetic active ingredient according to claim 13, wherein the cosmetic active ingredient is useful for preserving the pigmentation of hair and/or for improving the structural quality of hair.

15. The cosmetic active ingredient according to claim 13, wherein the cosmetic active ingredient is useful for reducing the number of gray hairs.

16. A cosmetic composition comprising at least 0.1 wt. % of an active ingredient according to claim 1.

17. The cosmetic composition according to claim 16, characterized in that it is provided in the form of shampoo, hair gel, hair lotion, hair mask, hair conditioner, conditioner, hair cream.

18. The cosmetic composition according to claim 16, wherein the cosmetic composition is useful for preventing and/or combating graying of the hair.

19. A method for obtaining an active ingredient according to claim 1, characterized in that it comprises the following steps:
   a) solubilizing powdered seeds of *Avena strigosa* in water followed by enzymatic hydrolyses and enzymatic inactivation by heat treatment,
   b) solubilizing powdered roots of *Ononis spinosa* in a Butylene Glycol/water mixture,
   c) mixing products from steps a) and b),
   d) separating the soluble and insoluble phases, and
   e) filtration(s).

20. A method for the cosmetic treatment of the hair of a human being, to prevent and/or combat graying of the hair, characterized in that it consists in applying to the hair at least once a day a composition according to claim 16.

\* \* \* \* \*